United States Patent [19]

Makabe et al.

[11] 4,331,597
[45] May 25, 1982

[54] PENICILLIN COMPOUNDS

[75] Inventors: Osamu Makabe, Tokyo; Yasushi Murai, Yokosuka; Tuneo Okonogi; Masahiro Onodera, both of Yokohama; Takashi Yoshida; Shunzo Fukatsu, both of Tokyo, all of Japan

[73] Assignee: Meiji Seika Kaisha, Ltd., Tokyo, Japan

[21] Appl. No.: 193,317

[22] Filed: Oct. 2, 1980

[30] Foreign Application Priority Data

Oct. 2, 1979 [JP] Japan .................................. 54-126410

[51] Int. Cl.³ ............................................ C07D 499/70
[52] U.S. Cl. .................................. 260/239.1; 424/264; 546/288; 546/315; 546/318; 568/315; 568/337; 568/649
[58] Field of Search ...................................... 260/239.1

[56] References Cited

U.S. PATENT DOCUMENTS 4,053,470 10/1977 Doub et al. ...................... 260/239.1

*Primary Examiner*—Natalie Trousof
*Assistant Examiner*—Vera C. Clarke

*Attorney, Agent, or Firm*—Sughrue, Mion, Zinn, Macpeak and Seas

[57] ABSTRACT

Penicillin compounds and methods for the production thereof are described, said penicillin compounds being represented by the formula (I)

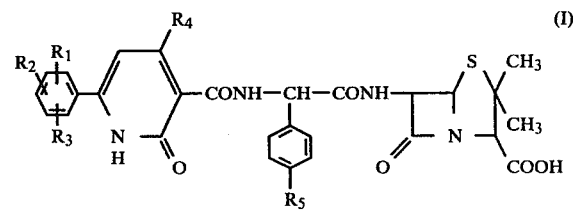

wherein $R_1$, $R_2$, and $R_3$ each represents hydrogen, a lower alkyl group, a halogen atom, a lower alkoxy group, a hydroxyl group, or a substituted or unsubstituted phenylalkoxy group except that $R_1$, $R_2$, and $R_3$ cannot all represent hydrogen simultaneously; $R_4$ represents hydrogen or a lower alkyl group; and $R_5$ represents hydrogen or a hydroxyl group.

5 Claims, No Drawings

PENICILLIN COMPOUNDS

BACKGROUND OF THE INVENTION

1. Field of the Invention

This invention relates to novel penicillin compounds and pharmaceutically acceptable salts thereof, and to a process for preparing such compounds and salts. More particularly, this invention relates to penicillin compounds of the following formula (I), or pharmaceutically acceptable salts thereof, and to processes for preparing such compounds or salts.

2. Description of the Prior Art

Penicillin type compounds have antibacterial activities and many derivatives thereof have been produced hitherto.

Recently, a research on penicillin compounds aims to develop a useful compound against Gram-negative bacteria, especially *Pseudomonas aeruginosa*, and bacteria which have a lactamase. However, very few penicillin compounds exhibit satisfactory antibacterial activity against said bacteria. For example, resembled compounds of this invention are disclosed in *Journal of Antibiotics*, Vol. 32, No. 6, page 621 (1979), but do not exhibit satisfactory antibacterial activity against said bacteria.

SUMMARY OF THE INVENTION

According to this invention, novel penicillin compounds and pharmaceutically acceptable salts thereof are provided. The compounds can be represented by the formula (I)

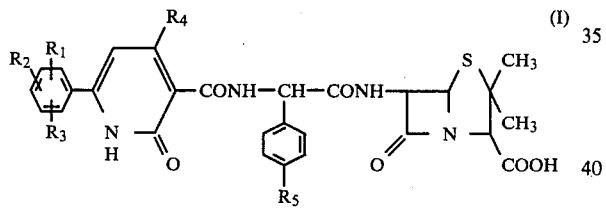

wherein $R_1$, $R_2$ and $R_3$ each represents hydrogen, a lower alkyl group, a halogen atom, a lower alkoxy group, hydroxyl group, or substituted or unsubstituted phenylalkoxy group, except that $R_1$, $R_2$ and $R_3$ cannot all be hydrogen simultaneously; $R_4$ represents hydrogen, or a lower alkyl group; $R_5$ represents hydrogen, or a hydroxyl group.

Further according to the invention, methods are provided for preparing compounds according to formula (I). Particularly, one method according to the invention provides compounds according to formula (I) wherein $R_5$ is a hydroxyl group, and a second method according to the invention provides compounds according to formula (I) wherein $R_5$ is either hydrogen or a hydroxyl group.

DETAILED DESCRIPTION OF THE INVENTION

In the formula (I), $R_1$, $R_2$, and $R_3$, which may be the same or different, can represent hydrogen; a lower alkyl group having from 1 to 4 carbon atoms, such as methyl, ethyl, n-propyl, i-propyl, n-butyl, i-butyl and t-butyl; a lower alkoxy group having from 1 to 4 carbon atoms, such as methoxy, ethoxy, propoxy and butoxy; a substituted or unsubstituted phenylalkoxy group (wherein the alkoxy moiety has from 1 to 3 carbon atoms and the substituent includes an alkyl group having from 1 to 4 carbon atoms, a halogen atom (such as chlorine and bromine), a nitro group, a formylamino group, and a lower alkoxy group having from 1 to 4 carbon atoms), such as phenylmethoxy, phenylethoxy, phenylpropoxy, dimethoxybenzyloxy, methoxybenzyloxy, formylaminobenzyloxy, and 3-methoxy-4-formylaminobenzyloxy; a halogen atom such as fluorine, chlorine, bromine and iodine; or a hydroxyl group, except that $R_1$, $R_2$, and $R_3$ cannot all be hydrogen simultaneously.

The substituent $R_4$ may, for example, be hydrogen or a lower alkyl group having from 1 to 4 carbon atoms, such as a methyl, ethyl, n-propyl, i-propyl, n-butyl, i-butyl or t-butyl group.

The compound of the formula (III), described below, i.e., a compound as in the formula (I) wherein $R_5$ is a hydroxyl group, can be produced by a method described hereinafter.

In a method according to the present invention, amoxycillin of the formula (A)

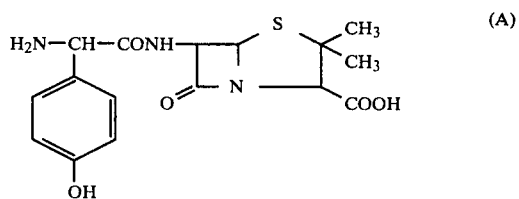

of which the functional groups (i.e., amino group and carboxyl group) may be protected or not, is reacted with a carboxylic acid of the formula (II)

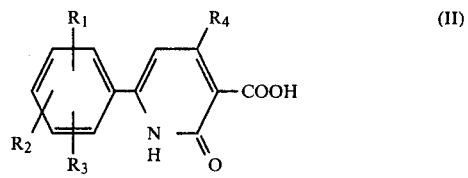

wherein $R_1$, $R_2$, $R_3$, and $R_4$ each has the same meaning as defined above, or a carboxylic reactive derivative thereof (such as acid halide, mixed acid anhydride, etc.), or a hydroxyl-protected derivative of the carboxylic acid or the carboxylic reactive derivative thereof when $R_1$, $R_2$ and/or $R_3$ represents hydroxyl group, thereby obtaining a penicillin compound of the formula (III)

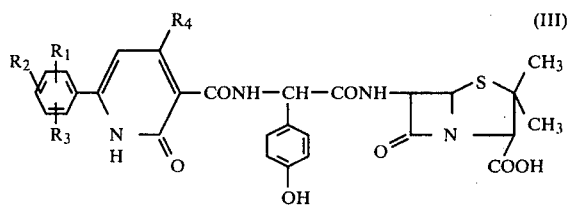

wherein $R_1$, $R_2$, $R_3$, and $R_4$ each has the same meaning as defined above.

This reaction can be carried out in a solvent in a known manner, thereby forming a CONH bond (peptide bond) between said amoxycillin of formula (A) and carboxylic acid of formula (II).

Particularly, this reaction may be conducted under conventional conditions for the production of polypeptides, penicillins or cephalosporins as described by Miklos Bodanszky et al., *Peptide Synthesis*, Interscience Publishers (1966), pp. 75-125 (reference 1), and E. H. Flynn, *Cephalosporins and Penicillins, Chemistry and Biology*, Academic Press (1972) (reference 2).

This reaction proceeds advantageously even if the amino group and carboxyl group of amoxycillin are not protected. In the reaction using amoxycillin of which amino group and carboxyl group are not protected, an organic solvent such as esters, ethers and amides can be used. Particularly, an aprotic polar organic solvent, such as dimethylformamide and diethylformamide, is advantageously used. The reaction can be carried out at a temperature of from about −50° C. to 100° C. for from about 30 minutes to 24 hours.

In the reaction between amoxycillin of the formula (A) and the carboxylic acid of the formula (II), amoxycillin protected in either or both of their amino and carboxyl groups may also advantageously be used.

The carboxyl group and amino group of amoxycillin can be protected by a trialkylsilylating agent. For example, in a case that amoxycillin must be reacted in an anhydrous condition, such as in an organic solvent, the unprotected amoxycillin can be dissolved in an organic solvent such as alkylhalogenide, and by means of treating with a trialkylsilylating agent such as trimethylchlorosilane or hexamethyldisilazane, the unprotected amoxycillin can be converted to a trimethylsilyl ester or N,O-bis-trimethylsilyl derivatives.

Benzhydrylester, benzylester, trichloroethylester, p-nitrobenzylester, alkoxymethylester, t-butylester and the like may be used for the protection of the carboxyl group of amoxycillin.

A protection of amino group of amoxycillin is conducted according to a method described in *Cephalosporins and Penicillins, Chemistry and Biology*, p. 81, Academic Press (1972). For example, an amino group is suitably protected by t-butoxycarbonyl group, enamine-form protecting group, or silazane-type protecting group.

When a hydroxyl group is present in $R_1$, $R_2$ and/or $R_3$ of the carboxylic acid of the formula (II) or the carboxylic reactive derivative thereof, the hydroxyl group is protected by p-nitrobenzylether, p-methoxybenzylether, methoxymethylether, methoxyethylether, pyranylether or phenacylether.

The penicillin compounds obtained according to this invention may preferably be esterified, and the esterification products thus-obtained can be formulated and administered for improved bioavailability (e.g., oral absorption, intestinal absorption, and formulation stability properties). For this purpose, the esterification is effected either by esterification of the final product or by subjecting the esterified amoxycillin to a reaction to form a peptide bond. In the latter case, there is an advantage in that the amoxycillin esters can react under anhydrous conditions because of their solubility in organic solvents. These esters, for example, may be an alkanoyloxy alkylester such as pivaloyloxymethylester and 1-acetoxy-1-ethylesters, phthalidylester, phenylester and indanylester.

Reactive derivatives at the carboxyl group of carboxylic acid of the formula (II) that can be used in this invention can be prepared in a known manner (e.g., references 1 and 2). The typical examples of these compounds are an acid-halide such as acid-chloride, mixed acid anhydride obtained from several organic acids and inorganic acids (sulfuric acid, phosphoric acid, hemialkylester of carbonic acid), active esters having several electrophilic alcoholic residues or phenol residues, active thioesters, active amides and pseudohalogenides such as acid-azide and sulfonate.

Examples of dehydration-condensing agents which provide reactive derivatives of the carboxyl or amino group, forming the peptide bond desired, may be carbodiimides, an alkoxyacetylene, Woodword's reagent, amidephosphates, cyanide phosphate, phosphorous esters, phosphorous anhydride, polyphosphoric esters, Willsmeier reagent, phosphorous ester halide and phosphorous halides.

The reactive derivatives of carboxyl group of carboxylic acid of the formula (II) and amoxycillin are allowed to react in the molar ratio of from 2:1 to 1:1 usually in an organic solvent containing water, an anhydrous organic solvent, or an aprotic polar organic solvent, at a temperature of from −50° C. to 100° C. or in the range of the boiling point of said solvent for from 30 minutes to 24 hours to cause peptide bonding.

The reaction conditions are not restricted to such a range, and they may be selected appropriately according to the reagents used, the degree of activation required, the scale of the reaction, the solvent used, and so forth.

After the reaction, the product is isolated in a conventional manner, for example, using a solvent partition method, adsorption chromatography, ion-exchange chromatography, precipitation method, recrystallization or the combination thereof.

The compounds obtained, when they are esters as described above, can be used directly for the purpose of this invention, but if it is desired to obtain the compounds of the formula (I) from the protected products, they may be subjected to deesterification to convert them to the desired products.

The deesterification can be accomplished by hydrolysis in a neutral to acidic medium, reduction such as catalytic reduction and reduction with zinc dust, or deesterification with a strong acid (e.g., trifluoroacetic acid, formic acid, acetic acid, etc.) in such a mild condition as not to decompose penicillin compounds.

The penicillin compounds of the formula (I) can also be produced in another way, as described below.

That is, the protected or unprotected penicillin compounds of the formula (I) and the pharmaceutically acceptable salts thereof can be produced by a method which comprises reacting 6-aminopenicillanic acid or its derivatives protected either in both of the amino and carboxyl groups or only in the carboxyl group, which are represented by the formula (V)

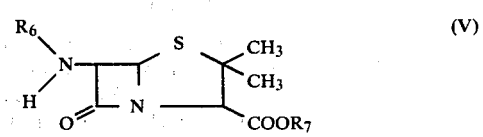

wherein $R_6$ is hydrogen or an amino-protecting group, $R_7$ is hydrogen or a carboxyl-protecting group, with a compound of the formula (IV)

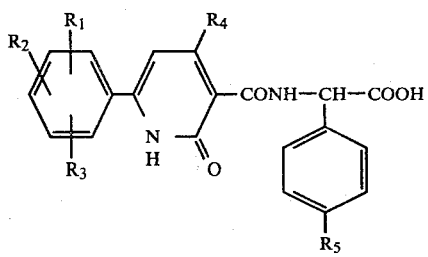

(IV)

wherein $R_1$, $R_2$, $R_3$, $R_4$, and $R_5$ each has the same meaning as defined above, or a reactive derivative thereof (at the carboxyl group) (such as acid halide, mixed acid anhydride, etc.), or a hydroxyl-protected derivative of the compound of formula (IV) or the reactive derivative thereof when $R_1$, $R_2$, $R_3$ and/or $R_5$ represents hydroxyl groups.

Reactive derivatives (at the carboxyl group) of the formula (IV) can be obtained in the same manner as mentioned previously with respect to the production of carboxyl reactive derivatives of the compound of formula (II).

The above second method according to this invention is a known method and can be carried out in the same manner as the method for the reaction between amoxycillin or a protected derivatives thereof and the carboxylic acid of the formula (II) as described above.

For the carboxyl- and amino-protected derivatives represented by the formula (V), kind of carboxyl-protecting and amino-protecting groups, and purpose and method of protection are the same as described for amoxycillin.

Further, for protection of hydroxyl group(s) being present in $R_1$, $R_2$, $R_3$ and/or $R_5$ of the compound of the formula (IV), the same hydroxyl-protecting groups as described above for the hydroxyl group of the carboxylic acid of the formula (II) can be used.

The ester compounds obtained by this method, if desired, can be subjected to deesterification as described above to provide the desired compounds.

Penicillin compounds obtained according to this invention may be converted into pharmaceutically acceptable salts in a known manner as described, for example, in *Cephalosporins and Penicillins, Chemistry and Biology*, Academic Press (1972). These salts include alkali metal salts such as sodium salt, potassium salt, calcium salt and magnesium salt; alkaline earth metal salts; salts with organic amines such as ethylamine, benzylamine, benzathine, dimethylbenzylamine, dibenzylamine, dicyclohexylamine, 2-hydroxyethylamine, triethylamine, and procaine; salts with amino acids such as lysine, glutamic acid, aspartic acid and arginine.

The compounds obtained according to this invention are novel and low-toxicity compounds which inhibit β-lactamase (penicillinase, cephalosporinase), show a wide range of antibiotic spectrum, and they also exhibit an antibacterial activity against Gram-negative bacilli resistant to known synthetic penicillins, particularly against glucose nonfermenting Gram-negative bacteria. Antimicrobial test (i.e., minimum inhibitory concentration test) on compounds obtained according to this invention was conducted according to the Japan chemotherapy method, using Apalcillin (PC-904) for comparison purposes.

The results are summarized in Table 1.

TABLE 1

Minimum Inhibitory Concentration(γ/ml) in Agar Dilution Method (Plate)

| Microorganism | Compound of Example 1 | Compound of Example 3 | PC-904 Apalcillin |
|---|---|---|---|
| *Staphylococcus aureus* 209PJC-1 | 0.39 | 0.39 | 0.39 |
| *Staphylococcus aureus* Smiths-424 | 0.39 | 0.20 | 0.39 |
| *Streptococcus faecalis* ATCC6633 | 3.13 | 3.13 | 6.25 |
| *Escherichia coli* 255 | 12.5 | 6.25 | 50 |
| *Escherichia coli* GN206 | 3.13 | 1.56 | 25 |
| *Citrobacter freundii* GN346 (CSase) | 6.25 | 1.56 | 12.5 |
| *Klebsiella pneumoniae* GN69 | 25 | 25 | 50 |
| *Proteus morganii* 1510 (CSase) | 100 | 50 | 100 |
| *Proteus vulgaris* OX19 | 0.39 | 0.39 | 0.39 |
| *Serratia marcescens* No. 1 | 0.78 | 1.56 | 1.56 |
| *Serratia species* GN629 (CSase) | 6.25 | 6.25 | 25 |
| *Pseudomonas aeruginosa* E-2 | 3.13 | 6.25 | 1.56 |
| *Pseudomonas aeruginosa* M-0002 | 0.78 | 3.13 | 0.78 |
| *Pseudomonas capacia* M-0501 | 12.5 | 3.13 | 12.5 |
| *Pseudomonas cepacia* M-0513 | 12.5 | 3.13 | 25 |
| *Pseudomonas maltophilia* 602 | 12.5 | 25 | 50 |

This invention is explained in more detail by the following examples showing the production of penicillin compounds according to the invention, as well as the production of intermediates therefor.

PREPARATION EXAMPLE 1

(1) 30 g of sodium methylate was suspended in 500 ml of isopropyl ether, to which a solution of 90 g of 3,4-dimethoxyacetophenone dissolved in 37 g of ethylformate was added while stirring and ice-cooling, and the suspension was further stirred for 2 hours at room temperature. The isopropyl ether was removed under reduced pressure, and the residue was dissolved in 500 ml water, to which 59 g of α-cyanoacetoamide and 22 ml of piperidine-acetic acid buffer (pH 8) were added.

The resulting mixture was heated to 110° C. for 7 hours and was, then, adjusted to pH 4 with acetic acid while ice-cooling.

The resulting precipitate was filtered off, washed with 200 ml water, and crystallized with 300 ml of ethanol followed by washing with 100 ml ether to obtain 41 g of 6-(3,4-dimethoxyphenyl)-3-cyano-1,2-dihydro-2-oxopyridine. m.p. 268°–270° C.

ir (nujol): 2250 cm$^{-1}$ (—CN)

(2) The 41 g of 6-(3,4-dimethoxyphenyl)-3-cyano-1,2-dihydro-2-oxopyridine was suspended in 300 ml of 25% aqueous potassium hydroxide and heated at 110° C. while stirring for 13 hours. While hot, the mixture was poured into 1 l of 6 N aqueous HCl, followed by stirring while cooling with ice.

The resulting precipitate was filtered off, washed with 500 ml water, followed by washing three times with 300 ml acetone. The precipitate was recrystallized from dimethylformamide to obtain 41 g of 6-(3,4-dimethoxyphenyl)-1,2-dihydro-2-oxonicotinic acid. m.p. 273° C. (decomposition).

ir (nujol): 1705 cm$^{-1}$ (carboxylic acid) 1632 cm$^{-1}$ (pyridone)

PREPARATION EXAMPLE 2

Synthesis of 6-[4-(3,4-dimethoxybenzyloxy)-3-methoxyphenyl]-2-oxopyridine-3-carboxylic acid

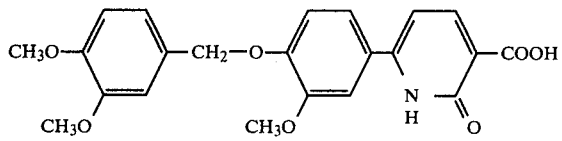

(1) 235 g of veratryl alcohol was dissolved in 1.4 l of absolute methylene chloride, to which 200 g of thionyl chloride was added dropwise while ice-cooling, and the mixture was stirred at room temperature overnight.

Dark brown and clear solution was poured into 1 l of ice-cold water and was adjusted to pH 7.0 with sodium bicarbonate. The methylene chloride layer was separated, washed with water, dehydrated and concentrated to dryness under reduced pressure to obtain 220 g of 3,4-dimethoxybenzyl chloride. m.p. 50°–51° C.

(2) 36 g of 60% sodium hydride solution was added to 200 ml of dried dimethylformamide with stirring under ice-cooling, to which 120 g of acetovanilline dissolved in 400 ml of anhydrous dimethylformamide was added dropwise. The mixture was allowed to react at room temperature under stirring for 1.5 hours, to which 200 g of 3,4-dimethoxybenzyl chloride dissolved in 400 ml anhydrous dimethylformamide was added and then heated to 110° C. while stirring overnight.

The dimethylformamide was removed under reduced pressure, the resulting residue was dissolved in 600 ml of methylene chloride, washed 3 times with 400 ml water, dehydrated and concentrated to obtain a syrup, which was then crystallized from ethanol, to yield 16.7 g of 4-(3,4-dimethoxybenzyloxy)-3-methoxyacetophenone. m.p. 119°–120° C.

(3) 12.6 g of 60% sodium hydride was suspended in 100 ml of absolute tetrahydrofuran and cooled with ice, to which 50 g of 4-(3,4-dimethoxybenzyloxy)-3-methoxyacetophenone and 17.6 g of ethylformate dissolved in 700 ml absolute tetrahydrofuran was added dropwise under stirring. The mixture solution was then heated at 50° C. while stirring overnight. The tetrahydrofuran solution was concentrated under reduced pressure to yield a powder which was then dissolved in 350 ml water, to which 20 g of α-cyanoacetoamide and 20 ml of piperidine-acetic acid buffer solution (pH 8) were added, and the solution was heated at 110° C. under stirring overnight.

The reaction solution was cooled with ice and adjusted to pH 4 with acetic acid to yield a precipitate which was filtered off, washed with 300 ml of acetone and recrystallized from dimethylformamide to obtain 16.7 g of 6-[4-(3,4-dimethoxybenzyloxy)-3-methoxyphenyl]-1,2-dihydro-2-oxo-3-cyanopyridine. m.p. 220°–221° C.

(4) 16.7 g of 6-[4-(3,4-dimethoxybenzyloxy)-3-methoxyphenyl]-1,2-dihydro-2-oxo-3-cyanopyridine was suspended in 400 ml of 25% aqueous potassium hydroxide and heated at 110° C. under stirring for 42 hours, to which 600 ml of 6 N aqueous HCl was poured and the solution was cooled with ice to yield powdered precipitate which was filtered off, washed with water, and recrystallized from methyl cellosolve to obtain 10 g of 6-[4-(3,4-dimethoxybenzyloxy)-3-methoxyphenyl]-1,2-dihydro-2-oxo-nicotinic acid. m.p. 217° to 218° C.

ir (nujol): 1710 cm$^{-1}$ (—COOH), 1640 cm$^{-1}$ (pyridone)

PREPARATION EXAMPLE 3

8 g of 6-(3,4-dimethoxyphenyl)-1,2-dihydro-2-oxonicotinic acid was dissolved in a mixture of 48 ml of dimethylformamide and 19 ml of pyridine, to which 10 g of p-nitrophenyltrifluoroacetate was added under ice-cooling followed by stirring at room temperature overnight to obtain a precipitate which was filtered off, washed with diethylether and recrystallized from dimethylsulfoxide to yield 7.9 g of p-nitrophenyl ester of 6-(3,4-dimethoxyphenyl)-1,2-dihydro-2-oxonicotinic acid.

ir (nujol): 1700 cm$^{-1}$ (ester), 1668 cm$^{-1}$ (pyridone), 1525, 1350 cm$^{-1}$ (nitro).

PREPARATION EXAMPLE 4

2.75 g of 6-(3,4-dimethoxyphenyl)-1,2-dihydro-2-oxonicotinic acid was suspended in 25 ml of dimethylformamide, to which 2 g of carbonyldiimidazole was added. After stirring at room temperature overnight, the resulting crystals were filtered off and washed with ether to obtain 2.8 g imidazole amide of 6-(3,4-dimethoxyphenyl)-1,2-dihydro-2-oxonicotinic acid.

ir (nujol): 1690 cm$^{-1}$ (amide), 1642 cm$^{-1}$ (pyridone).

PREPARATION EXAMPLE 5

55 g of 6-(3,4-dimethoxyphenyl)-1,2-dihydro-2-oxonicotinic acid was suspended in 550 ml of methylene chloride, to which 66.6 ml of triethylamine was added. After stirring at room temperature for 1 hour, the mixture was cooled to 5° C. and, 38 ml of ethyl-chloroformate was added dropwise thereto at a temperature ranging from 0° to 10° C.

After stirring for 2 hours, 46 g of N-hydroxysuccinic imide dissolved in 78 ml of dimethylformamide was added dropwise at a temperature from 5° to 10° C., followed by stirring at room temperature overnight.

The resulting precipitate was filtered off and washed with water and a little acetone. Recrystallization from 140 ml dimethylformamide yielded 45 g of succinic imide ester of 6-(3,4-dimethoxyphenyl)-1,2-dihydro-2-oxonicotinic acid.

ir (nujol): 1798, 1772 cm$^{-1}$ (amide), 1730 cm$^{-1}$ (ester), 1640 cm$^{-1}$ (pyridone).

PREPARATION EXAMPLE 6

2.0 g of D-p-hydroxyphenylglycine was suspended in a mixture of 20 ml dimethylformamide and 10 ml water, to which was further added 3.34 ml of triethylamine.

3.96 g of p-nitrophenyl ester of 6-(3,4-dimethoxyphenyl)-1,2-dihydro-2-oxonicotinic acid was added to the suspension under ice-cooling, and the reaction temperature was raised to room temperature followed by stirring overnight.

The solvent was removed under reduced pressure to obtain a syrup, which was suspended in 50 ml of water and was adjusted to pH 2 with aqueous 1 N HCl.

The resulting precipitates were filtered off and washed with water. Recrystallization from ethanol provided 4 g of 6-(3,4-dimethoxyphenyl)-1,2-dihydro-2- oxonicotinyl-p-hydroxyphenyl-glycine. m.p. 181°-183° C. (decomposition).

ir (nujol): 1700 cm$^{-1}$ (carboxylic acid), 1655, 1648 cm$^{-1}$ (pyridone, amide)

PREPARATION EXAMPLE 7

6 g of 6-[4-(3,4-dimethoxybenzyloxy)-3-methoxyphenyl]-1,2-dihydro-2-oxonicotinic acid was suspended in a mixture of 60 ml of dimethylformamide and 10 ml of pyridine, to which was added 5 g of p-nitrophenyltrifluoroacetate while ice-cooling, and the suspension was stirred at room temperature overnight. The precipitate was filtered off and washed with isopropylether.

Recrystallization from dimethylsulfoxide provided 6.2 g of p-nitrophenylester of 6-[4-(3,4-dimethoxybenzyloxy)-3-methoxyphenyl]-1,2-dihydro-2-oxonicotinic acid.

ir (nujol): 1710 cm$^{-1}$ (ester), 1650 cm$^{-1}$ (pyridone), 1515, 1345 cm$^{-1}$ (nitro).

EXAMPLE 1

3.7 g of succinic-imide ester of 6-(3,4-dimethoxyphenyl)-1,2-dihydro-2-oxonicotinic acid was suspended in 37 ml of anhydrous dimethyl acetoamide, to which was added 4.2 g of amoxycillin trihydrate under stirring, and the suspension was allowed to react under ice-cooling for 2 hours.

The reaction suspension was poured into 140 ml ice-water and adjusted to pH 2 with aqueous 1 N HCl.

The resulting precipitates were filtered off, washed with water followed by drying.

The precipitates were dissolved in 15 ml of methanol-dichloromethane (1:1) solvent, to which was further added sodium salt of 2-ethylhexanic acid and 45 ml of acetone to precipitate crystals which were filtered off to obtain 5.6 g of sodium salt of 6-(3,4-dimethoxyphenyl)-1,2-dihydro-2-oxonicotinyl amoxycillin.

ir (nujol): 1765 cm$^{-1}$ ($\beta$-lactam), 1655 cm$^{-1}$ (amide), 1605 cm$^{-1}$ (carboxylate).

n.m.r. (DMSO d-6) $\delta$ = 10.55 (d, 1H, —NH), 8.95 (d, 1H, —NH), 8.29, 6.80 (d, 1H, pyridone), 7.22, 6.70 (d, 2H, p-hydroxyphenyl),

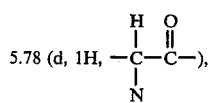

5.78 (d, 1H, —C(H)(N)—C(O)—), 5.35 (m, 2H, C$_6$—H, C$_5$—H), 3.93 (S, 1H, C$_3$—H), 3.85, 3.80 (S, 3H, —OMe), 1.55, 1.37 (S, 3H, Gem—CH$_3$)

EXAMPLE 2

1.1 g of 6-(3,4-dimethoxyphenyl)-1,2-dihydro-2-oxonicotinyl-D-(−)-p-hydroxyphenylglycine and 5 ml of absolute dimethylformamide were suspended in 25 ml of absolute tetrahydrofuran, to which 0.55 g of N-methylmorpholine was added.

The suspension was stirred at 0° C. for 15 minutes and cooled to −30° C., to which 0.59 g of ethyl chloroformate dissolved in 5 ml of absolute tetrahydrofuran was added dropwise and the suspension was allowed to react for 30 minutes.

877 mg of 6-amino-penicillanic acid triethylamine salt dissolved in 10 ml of dimethylformamide was added dropwise to the suspension, and the reaction temperature was raised gradually to room temperature, followed by stirring for 2 hours.

Solvent was removed under reduced pressure to obtain a syrup, which was suspended in 100 ml water and adjusted to pH 2 with aqueous 1 N HCl under stirring and ice-cooling.

The crude product precipitated was filtered off, washed with water and dissolved in an aqueous sodium bicarbonate to adjust the pH to 7. The solution was chromatographed on HP-50 resin (Daiaion HP-50, a product of Mitsubushi Chemical Industries Ltd.) which was then washed with water and eluted with 50% aqueous methanol, to yield 350 mg of the compound of Example 1.

EXAMPLE 3

2.9 g of amoxycillin trihydrate was suspended in 50 ml anhydrous dimethylformamide, to which 0.76 ml of triethylamine and 2.5 g of p-nitrophenylester of 6-[4-(3,4-dimethoxybenzyloxy)-3-methoxyphenyl]-1,2-dihydro-2-oxonicotinic acid were added under ice-cooling followed by stirring at room temperature overnight.

Solvent was removed under reduced pressure to obtain a syrup, which was suspended in water and adjusted to pH 2 with aqueous 1 N HCl. The precipitates were filtered off, washed with water and dissolved in aqueous sodium bicarbonate to adjust the pH to 7.0. The solution was chromatographed on HP-50 resin which was washed with water and eluted with aqueous 80% methanol to obtain 2 g of 6-[4-(3,4-dimethoxybenzyloxy)-3-methoxyphenyl]-1,2-dihydro-2-oxonicotinyl amoxycillin.

ir (nujol): 1760 cm$^{-1}$ ($\beta$-lactam) 1657 cm$^{-1}$ (amide) 1600 cm$^{-1}$ (carboxylate)

n.m.r. (DMSO d-6) $\delta$: 10.68 (d, 1H, NH), 8.90 (d, 1H, NH), 8.50, 6.80 (d, 1H, pyridone), 7.25, 6.70 (d, 1H, p-hydroxyphenyl), 7.20 (m, 6H, dimethoxyphenyl), 5.80 (d, 1H), 5.30 (m, 2H, C$_5$—H, C$_6$—H),

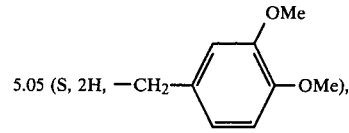

5.05 (S, 2H, —CH$_2$—C$_6$H$_3$(OMe)(OMe)), 3.92 (S, 1H, C$_3$—H), 3.85 (S, 3H, —OMe), 3.77 (S, 6H, —OMe), 1.56, 1.45 (S, 3H, Gem—CH$_3$).

EXAMPLES 4 TO 33

In an analogous manner as in the above example, compounds represented by formula (Ia)

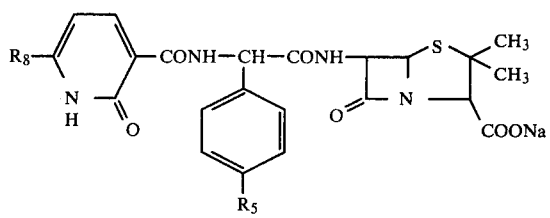

wherein R$_5$ and R$_8$ represent groups shown as below, were synthesized.

| Example No. | R5 | R8 | I.R. (cm⁻¹) |
|---|---|---|---|
| 4 | —H | H₃C—⟨O⟩— | 1760, 1660, 1600 |
| 5 | —OH | H₃C—⟨O⟩— | 1760, 1660, 1600 |
| 6 | —H | 2-CH₃-C₆H₄— | 1760, 1660, 1655, 1600 |
| 7 | —H | 3-CH₃-C₆H₄— | 1760, 1660, 1602 |
| 8 | —H | H₅C₂—⟨O⟩— | 1760, 1652, 1600 |
| 9 | —H | 2-Cl-C₆H₄— | 1761, 1662, 1610 |
| 10 | —H | 3-Cl-C₆H₄— | 1787, 1660, 1603 |
| 11 | —H | Cl—⟨O⟩— | 1760, 1656, 1600 |
| 12 | —H | F—⟨O⟩— | 1760, 1660, 1605 |
| 13 | —H | Br—⟨O⟩— | 1760, 1660, 1600 |
| 14 | —H | H₃CO—⟨O⟩— | 1761, 1662, 1605 |
| 15 | —OH | H₃CO—⟨O⟩— | 1760, 1660, 1600 |
| 16 | —H | 3-H₃CO-C₆H₄— | 1761, 1660, 1600 |
| 17 | —OH | 3-H₃CO-C₆H₄— | 1760, 1660, 1605 |
| 18 | —H | 2-OCH₃-C₆H₄— | 1762, 1633, 1600 |
| 19 | —OH | 2-OCH₃-C₆H₄— | 1760, 1660, 1600 |
| 20 | —H | 2,4-(H₃CO)₂-C₆H₃— | 1760, 1661, 1602 |
| 21 | —OH | 2,4-(H₃CO)₂-C₆H₃— | 1760, 1660, 1600 |
| 22 | —OH | 2,3-(H₃CO)₂-C₆H₃— | 1763, 1660, 1600 |
| 23 | —OH | 3,4-(H₃CO)₂-C₆H₃— | 1762, 1660, 1600 |
| 24 | —H | 3,4,5-(H₃CO)₃-C₆H₂— | 1765, 1660, 1605 |
| 25 | —H | 2,4,5-(H₃CO)₃-C₆H₂— | 1760, 1660, 1600 |
| 26 | —H | 3,5-(H₃C)₂-C₆H₃— | 1760, 1660, 1600 |
| 27 | —OH | 3,5-(H₃CO)₂-C₆H₃— | 1760, 1660, 1600 |
| 28 | —OH | 3,5-(H₃C)₂-C₆H₃— | 1761, 1660, 1600 |
| 29 | —OH | 3,5-(H₃CO)₂-C₆H₃—CH₂O—C₆H₄— | 1755, 1650, 1600 |
| 30 | —OH | H₃CO—C₆H₄—CH₂O—(3-CH₃O-C₆H₃)— | 1765, 1660, 1610 |
| 31 | —OH | HCONH—C₆H₄—CH₂O—C₆H₄— | 1760, 1660, 1600 |
| 32 | —OH | HCONH—(3-CH₃O-C₆H₃)—CH₂O—C₆H₄— | 1760, 1660, 1600 |
| 33 | —OH | HCONH—(3-CH₃O-C₆H₃)—CH₂O—(3-CH₃O-C₆H₃)— | 1760, 1660, 1600 |

While the invention has been described in detail and with reference to specific embodiments thereof, it will be apparent to one skilled in the art that various changes and modifications can be made therein without departing from the spirit and scope thereof.

What is claimed is:

1. A penicillin compound represented by the formula (I) and pharmaceutically acceptable salts thereof, wherein said formula (I) is

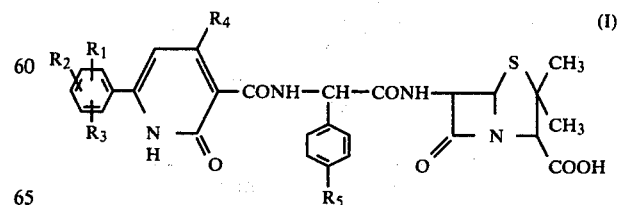

wherein $R_1$, $R_2$, and $R_3$ each represents hydrogen, a lower alkyl group, a halogen atom, a lower alkoxy group, a hydroxyl group, or a substituted or unsubstituted phenylalkoxy group, except that $R_1$, $R_2$, and $R_3$ cannot all represent hydrogen simultaneously; $R_4$ represents hydrogen or a lower alkyl group; and $R_5$ represents hydrogen or a hydroxyl group.

2. A penicillin compound as in claim 1 wherein $R_1$, $R_2$, and $R_3$ are selected from the group consisting of hydrogen, methyl, ethyl, n-propyl, i-propyl, n-butyl, i-butyl, t-butyl, methoxy, ethoxy, propoxy, butoxy, phenylmethoxy, phenylethoxy, phenylpropoxy, dimethoxybenzyloxy, methoxybenzyloxy, formylaminobenzyloxy, 3-methoxy-4-formylamino-benzyloxy, fluorine, chlorine, bromine, iodine, and hydroxyl groups.

3. A penicillin compound as in claim 1 wherein $R_4$ is selected from the group consisting of hydrogen, methyl, ethyl, n-propyl, i-propyl, n-butyl, i-butyl, and t-butyl groups.

4. 6-(3,4-Dimethoxyphenyl)-1,2-dihydro-2-oxonicotinyl amoxycillin and pharmaceutically acceptable salts thereof according to claim 1.

5. 6-[4-(3,4-Dimethoxybenzyloxy)-3-methoxyphenyl]-1,2-dihydro-2-oxonicotinyl amoxycillin and pharmaceutically acceptable salts thereof according to claim 1.

* * * * *